(12) United States Patent
Commuri (10) Patent No.: US 12,404,638 B2
(45) Date of Patent: Sep. 2, 2025

(54) RETROFIT INTELLIGENT COMPACTION ANALYZER

(71) Applicant: NEVADA RESEARCH & INNOVATION CORPORATION, Reno, NV (US)

(72) Inventor: Sesh Commuri, Reno, NV (US)

(73) Assignee: NEVADA RESEARCH & INNOVATION CORPORATION, Reno, NV (US)

( * ) Notice: Subject to any disclaimer, the term of this patent is extended or adjusted under 35 U.S.C. 154(b) by 692 days.

(21) Appl. No.: 17/782,329

(22) PCT Filed: Dec. 18, 2020

(86) PCT No.: PCT/US2020/066077
§ 371 (c)(1),
(2) Date: Jun. 3, 2022

(87) PCT Pub. No.: WO2021/133680
PCT Pub. Date: Jul. 1, 2021

(65) Prior Publication Data
US 2023/0020213 A1  Jan. 19, 2023

Related U.S. Application Data

(60) Provisional application No. 62/952,944, filed on Dec. 23, 2019.

(51) Int. Cl.
*E01C 19/28* (2006.01)
*G01N 33/42* (2006.01)

(52) U.S. Cl.
CPC ........... *E01C 19/288* (2013.01); *G01N 33/42* (2013.01)

(58) Field of Classification Search
None
See application file for complete search history.

(56) References Cited

U.S. PATENT DOCUMENTS 6,122,601 A   9/2000  Swanson et al.
8,099,218 B2  1/2012  Glee et al.
(Continued)

FOREIGN PATENT DOCUMENTS

JP   2000-110111 A   4/2000
WO   2017095239 A1   6/2017

OTHER PUBLICATIONS

Chinese Office Action dated Sep. 27, 2024 which was issued in connection with Chinese Application No. 202080089360.7, (23pages). English machine translation provided.
(Continued)

*Primary Examiner* — Matthew G Marini
(74) *Attorney, Agent, or Firm* — Buckley, Maschoff & Talwalker LLC (57) ABSTRACT

A method, apparatus and system for providing an estimate of the level of compaction of a layer of pavement materials in real time. In some embodiments, a Retrofit Intelligent Compaction Analyzer (RICA) processor of a RICA device receives vibrational energy data from a sensor module which corresponds to impact responses of a drum of a roller machine during compaction of a pavement material over a section of pavement. The RICA processor also receives temperature data from the sensor module, determines an estimated level of compaction in real time of the section of pavement based on the vibrational energy data, pavement material characteristics data and the temperature data, and displays a density level percentage of the section of pavement on a display device for viewing by an operator of the roller machine.

16 Claims, 9 Drawing Sheets (56) References Cited

U.S. PATENT DOCUMENTS

2010/0017269 A1    1/2010   Giannini et al.
2010/0172696 A1    7/2010   Commuri
2011/0293369 A9   12/2011   Commuri

OTHER PUBLICATIONS

European Search Report dated Nov. 29, 2023 which was issued in connection with European Application No. 20907945.8 , (5 pages).
Japanese Office Action dated Sep. 5, 2023 which was issued in connection with Japanese Application No. 2022-564094, (9 pages). English machine translation provided.
Canadian Examination Report date 28, Sep. 2023 which was issued in connection with Canadian Patent Application No. 3,161,259.
Australian First Examination Report dated Mar. 31, 2023 which was issued in connection with Australian Application No. 2020412458, (4 pages).
"The International Search Report and Written Opinion" dated Mar. 23, 2021 which is issued in connection with PCT Application No. PCT/US2020/066077.
Japanese Office Action dated Dec. 5, 2023 which was issued in connection with Japanese Application No. JP 2022-564094, (11 pages).

RETROFIT INTELLIGENT COMPACTION ANALYZER

CROSS REFERENCE TO RELATED APPLICATIONS

This application is a U.S. National Stage patent application and claims the benefit of International Patent Application No. PCT/US20/66077 filed on Dec. 18, 2020, which claims the benefit of U.S. Provisional Patent Application No. 62/952,944 filed on Dec. 23, 2019, the contents of which are hereby incorporated by reference for all purposes.

FIELD OF THE INVENTION

Methods and apparatus for providing an estimate of the level of compaction during the compaction of pavement materials. Specifically, a retrofit intelligent compaction analyzer apparatus that can be retrofit to a vibratory compactor to provide estimates of the level of compaction of the pavement materials to an operator in real time. The compaction level estimates may provide density information in a format suitable for the operator of the compactor to understand and use to determine when adequate compaction has been achieved for a particular portion of a roadway during its construction.

BACKGROUND

Asphalt pavements are designed to carry traffic loads with minimum physical deterioration, maximum safety, and maximum ride comfort. Based on the design, an asphalt pavement is expected to bear traffic loading up to 30 million Equivalent Single Axle Loads (ESALs) over a 20-year life span.

A finished asphalt pavement is the result of a multistage process: from pavement design according to specifications and then to construction and quality assurance. The process begins with the design of the pavement according to the specifications based on the type of the road, traffic volumes, intended use, condition of the base layer, and the seasonal variations that the road has to withstand. Next steps include production of hot mix asphalt according to the design, transportation of the asphalt mix from the production facility to the construction site, placement of the mix, and then compaction of the mix using vibratory rollers to achieve the desired density.

Compaction is one of the most important steps in pavement construction as it can significantly affect the quality of the constructed pavement. Compaction increases the interlocking between aggregates and thereby reduces the air void content between aggregates. Studies suggest that for optimal performance of asphalt pavement the air void content is required to be between three percent (3%) and five percent (5%). Under-compacted pavements deteriorate early due to increased fatigue. Experiments show that reducing the air-void content of a given asphalt-concrete mix from eight percent (8%) to five percent (5%) can improve the fatigue life of the pavement by one-hundred percent (100%). Proper compaction also reduces permeability of the mix, and increases the load bearing capacity, increases resistance to deformation (or rutting), and increases the durability of the pavement. Proper compaction also reduces deterioration of the pavement due to rutting, oxidization, moisture damage, distortion, and disintegration or raveling of the pavement. Therefore, proper compaction of asphalt pavement is necessary to achieve its designed properties and to ensure its performance and longevity.

In the asphalt paving process for roadways, various gradations of aggregate can be used. The aggregates are typically mixed with asphalt cement (tar) and sand, and then heated to between about 150 degrees Centigrade)(C.° and 169 C.°. A paver lays down the hot asphalt mix and then levels the asphalt mix using a series of augers and scrapers. As initially laid down to form a roadway, the asphalt material is not dense enough to adequately support vehicle traffic due to air voids which form in the asphalt mix. Thus, a roller machine is typically utilized to make a number of passes over the layer of asphalt material (the "asphalt mat"), with an operator driving the roller machine back and forth over the asphalt material, or otherwise creating sufficient compaction to form asphalt having a desired strength for the road surface (or to form an individual pavement layer).

Road rollers achieve compaction by applying compaction energy to the material (e.g., soil, asphalt, and the like) as the vibratory compactor traverses back and forth over the material. The compaction energy is typically applied by means of eccentric weights that rotate inside a drum of the vibratory compactor, or through a vibratory screed which also smooths out the surface of the roadway. In the United States, in order to satisfy State Department of Transportation (State DoT) material compaction requirements, it is typically necessary to achieve compaction of the asphalt mat to a desired level of stiffness without over-compacting the mix. In addition, it is known that excessive compaction can result in irreversible damage to the pavement or roadway.

Currently, there is no accepted quality assurance method for a State DoT to assess the stiffness of completed pavement. In order to assess the quality level of the asphalt mat, in many cases one or more roadway cores are extracted from completed pavement work after the asphalt has cooled down, and then tests are conducted on the cores to determine their volumetric properties and density. The underlying premise is that the density of the cores is related to the stiffness and all other variables being constant, the stiffness is directly influenced by the density. Early deterioration of pavements due to rutting, fatigue cracking, and other types of distresses may be attributed to inadequate stiffness achieved during the compaction process. Thus, State DoTs typically specify a target density of about 94% to 96% of the Theoretical Maximum Density (% TMD) of the asphalt mix as a metric for acceptance testing. In case of soil subgrades, the acceptance tests are usually specified in terms of density and moisture content.

Taking core measurements is expensive, time consuming, and may not be indicative of the overall compaction achieved unless such core measurements are taken at a large number of points distributed in a grid fashion, which is difficult to achieve in the field and which may also be unduly expensive. Moreover, different states of the United States and/or different counties and/or jurisdictions or municipalities may each have different compaction density requirements. In addition, since pavement density acceptance tests are usually performed after the roadway construction has been completed there is no opportunity to achieve additional compaction if that is desired. But failure to meet the target density requirement is unacceptable to most State DoT's, and thus remedial measures are taken when necessary, which can result in significant cost overruns.

Several Intelligent Compaction (IC) technologies have been introduced recently by manufacturers of vibratory compactors or roller machines which attempt to achieve uniform compaction of both soil and aggregate bases by varying compactor machine parameters (such as amplitude and frequency of vibrations, vectoring of the thrust, etc.) during the compaction process. Dynamic control of the roller machine parameters allows for the application of the vibratory energy to only under-compacted areas in an attempt to prevent over-compaction of other areas and thus achieve uniform compaction of the pavement layer. While these intelligent compaction (IC) technologies may hold some future promise, their overall performance has yet to be fully evaluated in the field. In addition, many of these IC products require construction companies to purchase new vibratory compactors that are equipped with the technology which is an expensive proposition.

Accordingly, a need exists for tools and/or techniques which can be retrofit to existing vibratory compactor or roller machines that can enable operators to estimate the level of compaction in real-time during roadway construction in order to determine if any corrective steps should be undertaken to achieve a desired quality level of compaction as the roadway is being constructed.

BRIEF DESCRIPTION OF THE DRAWINGS

Features and advantages of some embodiments of the present disclosure, and the manner in which the same are accomplished, will become more readily apparent upon consideration of the following detailed description taken in conjunction with the accompanying drawings, which illustrate preferred and example embodiments and which are not necessarily drawn to scale, wherein.

DETAILED DESCRIPTION

Reference will now be made in detail to various novel embodiments, examples of which are illustrated in the accompanying drawings. The drawings and descriptions thereof are not intended to limit the invention to any particular embodiment(s). On the contrary, the descriptions provided herein are intended to cover alternatives, modifications, and equivalents thereof. In the following description, numerous specific details are set forth in order to provide a thorough understanding of the various embodiments, but some or all of the embodiments may be practiced without some or all of the specific details. In other instances, well-known process operations have not been described in detail in order not to unnecessarily obscure novel aspects.

In general, and for the purposes of introducing concepts of embodiments of the present disclosure, disclosed herein are methods and apparatus for providing an estimate of the level of compaction (or density) of pavement materials in real time to an operator of a roller machine during the compaction process. In an embodiment, a retrofit intelligent compaction analyzer (RICA) device is retrofit to a roller machine or vibratory roller. The RICA device utilizes data from a variety of sensors to generate compaction level estimates in real time to an operator of the roller machine of the pavement material being used to build a roadway. In some embodiments, the compaction level estimates provide density and/or stiffness information in a format suitable for the operator of the roller machine to understand and to determine when adequate compaction has been achieved for a particular portion of the roadway. It should be understood that, although the present disclosure includes examples concerning compaction of asphalt material and/or pavement during construction of roadways, the disclosed methods, apparatus and systems may be used for estimating the stiffness information of any bed of material such as soil that is being compacted.

Compactability of asphalt mix depends on several factors related to the environment, the mix properties and the construction process. These factors include the temperature of the asphalt mix at laydown, the thickness of the layer, the temperature and firmness of the underlying layer, the ambient temperature, the velocity and humidity of the air, and solar radiation levels. For example, the minimum layer thickness must be three to four times the nominal maximum aggregate size in order to allow the aggregates to realign and interlock during compaction. The mix also has to be above a certain temperature, called the cessation temperature, for it to be pliable. Unless these factors are addressed during the construction process, they can lead to under-compaction and/or non-uniform compaction of the pavement.

Thus, a well-designed and controlled compaction process is essential in order to achieve good quality and long-lasting asphalt pavements. On one hand under-compaction will leave a high percentage of air voids in the pavement, making it susceptible to moisture infiltration, oxidation and cracking. On the other hand, over-compaction will result in very low air voids that could result in asphalt bleeding into the pavement during hot weather conditions. Over-compaction could also result in the crushing of aggregates, thus altering the mechanical properties of the pavement. Therefore, poorly compacted pavements do not perform up to design specifications and are subject to early degradation and deterioration. Non-durable paved roads are very expensive to repair and maintain and contribute to traffic congestion that adds to environmentally polluting car, bus and truck emissions.

As mentioned above, traditional roadway compaction involves a vibratory roller moving at a constant speed and applying vibratory force of constant amplitude and frequency. The vibratory roller or compactor applies both static and dynamic forces (weight and vibration) in order to increase the interlocking between the aggregates and thereby reduce the air voids in the compacted mix. In addition to the mix and environmental conditions, the compaction that is achieved also depends on the type of rollers, the number of rollers, and the rolling pattern used during the compaction process.

One of the goals of the mechanistic design of asphalt pavements is to address the long term performance of the pavements. The stiffness of the pavement is a key design factor as it directly impacts the load bearing capability of the road. Further, early deterioration of the pavements due to rutting or fatigue cracking can easily be traced to inadequate stiffness. The National Cooperative Highway Research Program (NCHRP) Project I-37A ("Development of the 2002 Guide for the Design of New and Rehabilitated Pavement Structures") recommends the use of dynamic modulus as a measure of stiffness in the mechanistic design of pavements. While the dependence of the pavement performance on stiffness is well known, this parameter is rarely measured during the construction of the pavement. Instead, current quality control in the field during the construction of asphalt pavements focuses on the measurement of density of the finished pavement at specific locations.

Methods and apparatus described herein provide a good quality-control mechanism for use by an operator of a vibratory roller machine during the paving process that is representative of the quality of the entire pavement in real time. In disclosed embodiments, an operator of a vibratory roller machine utilizes the retrofit intelligent compaction analyzer (RICA) device to identify and correct many of the issues mentioned above during laying of the pavement, thus leading to an improved quality of the pavement so that the pavement can last for its design lifetime. Such quality-control operation during the construction of the pavement not only advantageously improves the overall performance of the paving process but also beneficially results in lower construction costs and lower maintenance costs.

Figure 1:
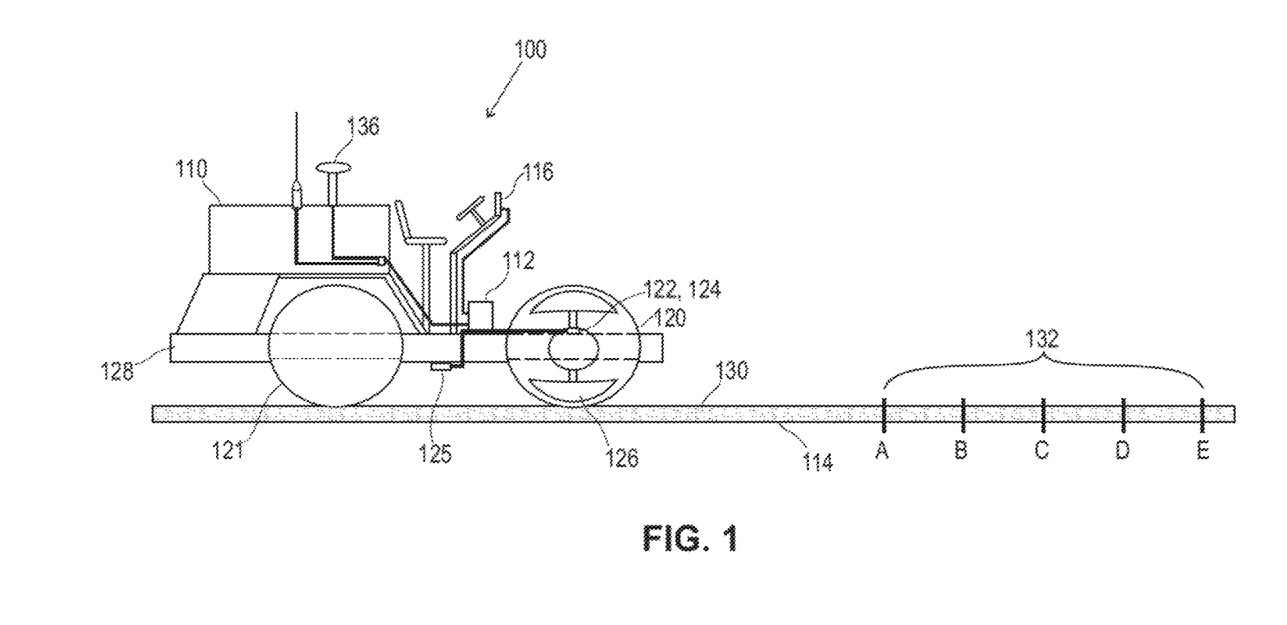
FIG. 1 is a block diagram of a vibratory compactor in accordance with embodiments of the present disclosure.

FIG. 1 is a schematic diagram 100 of a vibratory compactor or roller machine 110 that is retrofit with a Retrofit Intelligent Compaction Analyzer (RICA) device 112 that can measure the density of portions or sections of an asphalt pavement or roadway 114 continuously in real time, over the entire length of the pavement during its construction. In some embodiments, the RICA device 112 does not control any aspect of the roller machine 110 behavior and may be a stand-alone device that can be retrofitted onto any type of existing vibratory compactor. In embodiments described herein, the RICA device 112 obtains real-time measurements associated with the density of the asphalt mat at a plurality of locations on the pavement or roadway under construction, determines an estimated level of compaction, and then displays estimated level of compaction information to an operator of the roller machine 110 in a format that is understandable to the operator. The roller operator then uses the real-time measurement information to operate the roller machine in a manner to ensure uniform compaction, address under-compaction, and avoid over-compaction of the pavement or roadway.

Referring again to FIG. 1, in some embodiments the vibratory compactor or roller machine 110 includes a forward drum 120 and a rear drum 121. The forward drum 120 includes an eccentric weight 126 mounted therein, and in some implementations the forward drum 120 and the rear drum 121 both include eccentric weights 126 mounted therein. The eccentric weight 126 is rotated by motors (not shown), so that the rotation of the weight 126 within the drum 120 causes an impact at a contact point between the drum 120 and the pavement surface 130. The pavement surface 130 may be comprised of Hot Mix Asphalt (HMA), and may also be referred to as an asphalt mat. The spacing between impacts at the contact points is a function of the speed of the roller machine as the roller machine 110 moves along the pavement and the speed of the eccentric weights 126. For example, in some roller machine implementations there may be approximately ten to twelve (10-12) impulses or impacts per linear foot.

In some embodiments, the RICA device 112 is operably connected to a sensor module 122 mounted to the frame 128 of the vibratory roller 110. The sensor module 122 may be operably connected to accelerometers 124 capable of measuring 10 g acceleration (or 98.07 meters per second squared; 98.07 m/s$^2$) up to a frequency of 10 kilohertz (kHz), and may be operably connected to one or more infrared (IR) temperature sensors 125 that are shown here attached to an underside portion of the frame 128. The IR temperature sensors 125 measure the surface temperature of the pavement surface 130. Thus, in some implementations during operation of the roller machine 110 the sensor module 122 measures the vibrations of the vibratory compactor 110 and the IR temperature sensors 125 measure the surface temperature of the asphalt mat 130. Accordingly, the sensors 124, 125 associated with the sensor module 122 essentially comprise a real-time data acquisition system.

Figure 8:
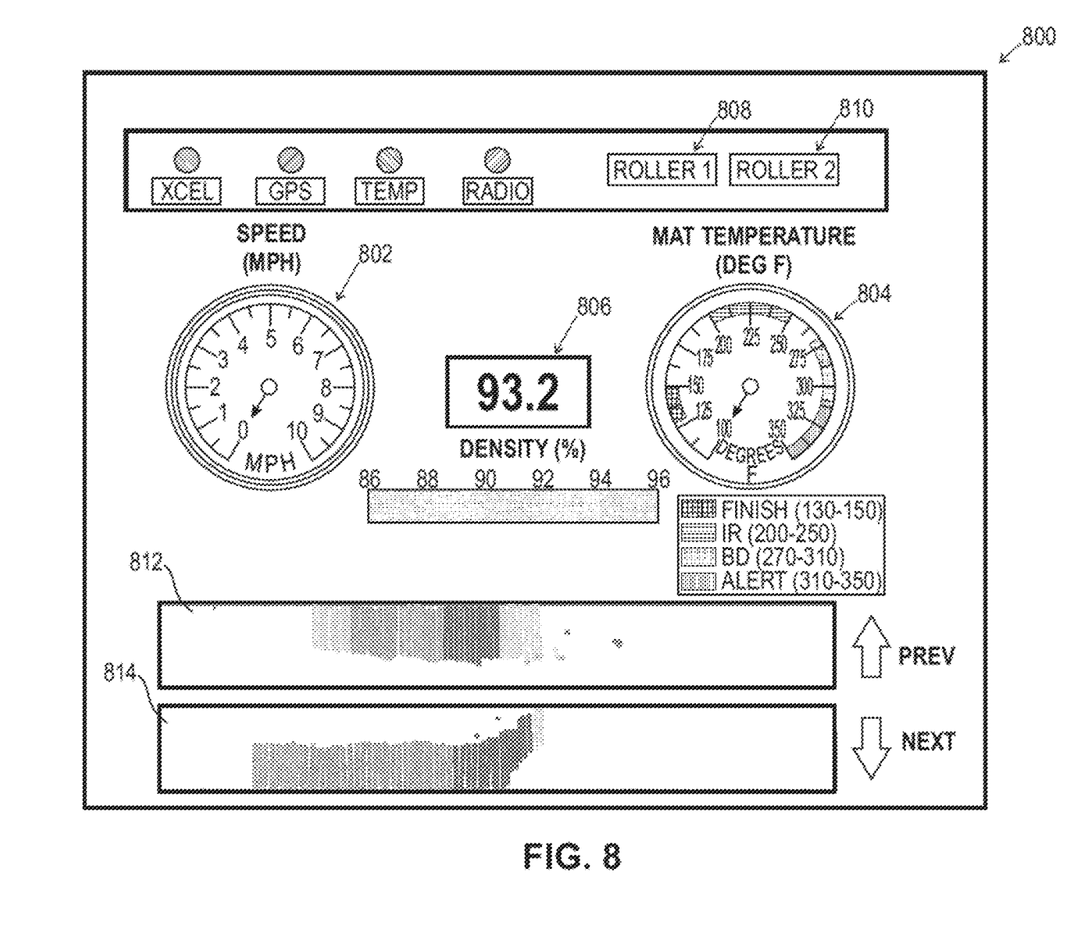
FIG. 8 shows a display screen of a Retrofit Intelligent Compaction Analyzer (RICA) device which may be provided to an operator of a vibratory compactor or roller machine in accordance with embodiments of the disclosure.

The RICA device 112 may be a specially designed computer, or may be a modified or unmodified laptop computer or tablet computer, having a display screen 116 (which may be a touchscreen) and a memory or storage device (not shown) including computer executable instructions for providing a graphical user interface (GUI) (an example is shown in FIG. 8) for viewing and use by the operator of the vibratory roller 110. The operator may utilize the GUI, for example, to specify and/or control the amplitude and frequency of the vibration motors of the roller machine, and to input data such as asphalt mat properties which may include, for example, the mix type and lift thickness. The GUI may also be utilized by the operator to enter other initial input parameters and the like data, and also to view data such as sensor module output data.

In some embodiments, a global positioning system (GPS) 136 is mounted to the vibratory roller 110. The GPS 136 provides data indicating the location of the vibratory roller 110 as it moves during roadway construction, for example, which location data can be used by the RICA device 112 so that the location of the generated densities of one or more roadway sections A-B, B-C, C-D and/or D-E of a roadway portion 132, for example, will be noted and/or known.

The RICA device 112 shown in FIG. 1 functions on the premise that the vibratory roller 110 and the underlying pavement material of a roadway 114, for example a Hot Mix Asphalt (HMA), form a coupled system. Thus, the response of vibratory roller 110 is determined by the frequency of its vibratory motors and the natural vibratory modes of the coupled system. Compaction of an asphalt mat 130 increases its stiffness and as a consequence, the vibrations of the compactor can be altered for different sections A-B, B-C, C-D and/or D-E as required to achieve a specified or desired compaction quality. The knowledge of the properties of the pavement material and the vibration spectrum of the compactor machine 110 can therefore be used to estimate the compaction quality of the asphalt mat.

As mentioned above, quality specifications for HMA are generally specified as a percentage of air voids so that, for example, 100% density means no air voids exist, and 90% density means 10% air voids exist. Thus, since the quality specifications are usually specified as percentage air void content or as a percentage of the Theoretical Maximum Density (TMD) of the asphalt mat, in some embodiments the RICA device 112 estimates the compacted density of the pavement for particular portions of the roadway during construction and then displays percentages (See item 806 in FIG. 8) on a display screen for viewing by the roller device operator. In embodiments described herein, the estimates of the compacted density of the pavement are displayed in real time so that the operator of the roller machine 110 can decide whether or not a particular roadway section needs additional compacting.

Figure 2:
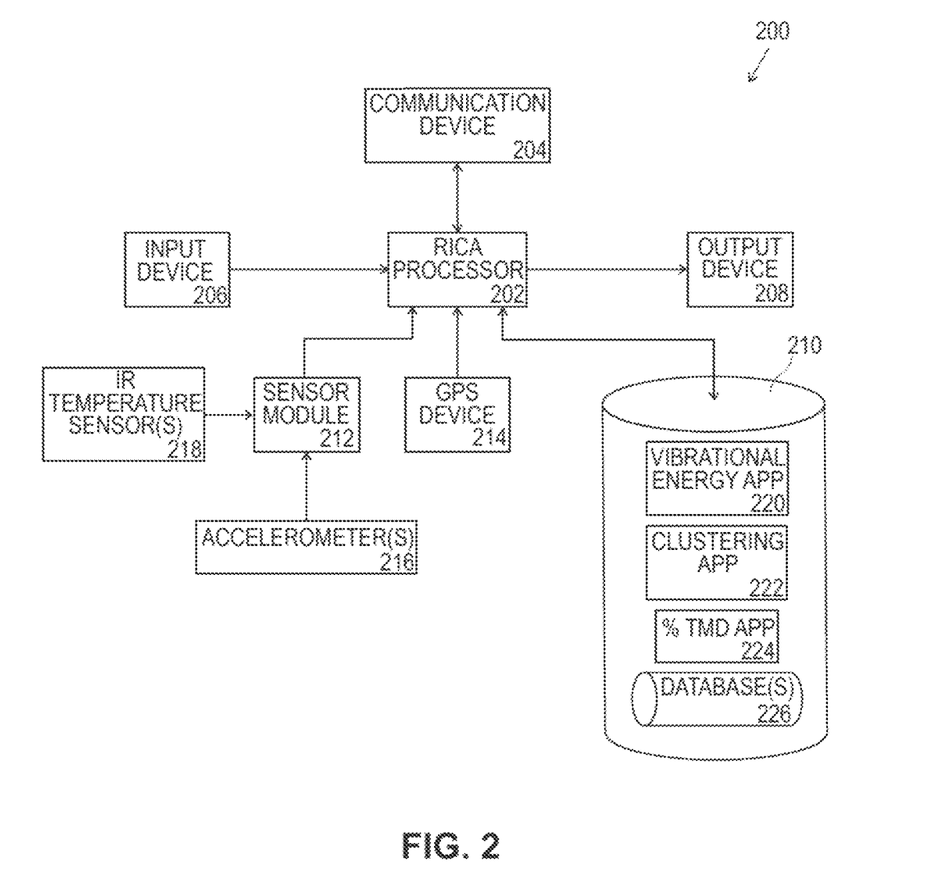
FIG. 2 is a block diagram of the different modules of an embodiment of a Retrofit Intelligent Compaction Analyzer (RICA) in accordance with the disclosure.

FIG. 2 is a block diagram illustrating an example embodiment of a Retrofit Intelligent Compaction Analyzer (RICA) device 200 in accordance with aspects of the present disclosure. The RICA device 200 may include standard components and/or custom-designed and/or proprietary components in terms of its hardware and/or architecture and may be controlled by software and/or computer program instructions to cause it to function as described herein. For example, the RICA device 200 may include server computer hardware.

As shown in FIG. 2, the RICA device 200 may include a RICA processor 202 operatively coupled to a communication device 204, an input device 206, an output device 208, and a storage device 210. The RICA processor 202, which may constitute one or more microprocessors, is also operatively coupled to a sensor module 212 and to a Global Positioning System (GPS) device 214. In some embodiments, the sensor module 212 includes one or more accelerometers 216 and one or more infrared (IR) temperature sensors 218. The RICA processor 202 operates to execute processor-executable steps, contained in program instructions described below, so as to control the RICA device 200 to provide desired functionality.

In some embodiments, the communication device 204 may be used to facilitate communication with, for example, other devices (such as server computers or handheld devices, such as tablet computers and/or smartphones, which may be operated by construction personnel) and/or to communicate with one or more other rollers operated by different operators. For example, communication device 204 may comprise numerous communication ports (not separately shown) to allow the RICA device 200 to communicate simultaneously with a number of other computers and other devices, including communications as required to monitor and/or record compaction level data estimates related to the density and/or stiffness of the soil, pavement or roadway beneath the roller machine being driven by the operator and/or to monitor compaction level data estimates of pavement or roadway beneath a second roller machine being operated by a different, second operator. Such operation would ensure that two or more operators can work in tandem to achieve a desired compaction level for a particular portion or portions of a roadway. Thus, the communication device may be configured for wireless communications and/or wired communications via various different types of networks, such as the Internet, and/or for communication via dedicated radio links and the like.

The input device 206 may include one or more of any type of peripheral device typically used to input data into a computer. For example, the input device 206 may include such components as a keyboard, a mouse and/or a microphone. The output device 208 may be, for example, a display component and/or a speaker and/or a printer. In some embodiments, the input device 206 and the output 208 comprise a touch screen.

Storage device 210 may comprise any appropriate information storage device, including combinations of magnetic storage devices (e.g., hard disk drives), optical storage devices such as CDs and/or DVDs, and/or semiconductor memory devices such as Random Access Memory (RAM) devices and Read Only Memory (ROM) devices, as well as flash memory and/or solid state drives (SSDs) and the like. Any one or more of such information storage devices may be considered to be a non-transitory computer-readable storage medium or computer usable medium or memory.

Storage device 210 stores one or more computer programs for controlling the RICA device 200. The programs comprise program instructions (which may be referred to as computer readable program code means) that contain processor-executable process steps of the RICA device 200, executed by the RICA processor 202 to cause the RICA device 200 to function as described herein. For example, the programs may include one or more conventional operating systems (not shown) that control the RICA processor 202 to manage and coordinate activities and sharing of resources in the RICA device 200, and to serve as a host for application programs that run on the RICA device 200. In addition, the storage device 210 may store a vibrational energy application 220 which utilizes fundamental frequency data and amplitude data obtained from sensors related to the vibrations of the roller drum during compaction of a roadway as the roller drum moves in both the forward and backward directions over the pavement, filters accelerometer data from one or more of the accelerometers 216, and extracts the average vibrational energy data at each of the harmonics. In addition, the storage device may include a clustering application 222 which controls the RICA processor to normalize the average energy of the harmonics in the accelerometer data and to group the energy into a pre-specified or predetermined number of groups. In some embodiments, the storage device 210 may also store a percentage Theoretical Maximum Density (% TMD) application 224 which controls the RICA processor to relate an estimated level of compaction to one or more density measurements determined from cores that have been extracted from known locations, and to provide output data which may be used to display one or more output graphs (not shown) to the operator of the roller machine in real time as the roller machine is being operated.

The storage device 210 may also store, and the RICA device 200 may also execute, other programs, which are not shown. For example, such programs may include a compaction density estimate reporting application, which controls the RICA processor 202 to transmit a density report to a remote server computer (not shown) via the communications device 204 concerning a predetermined length of roadway. Other programs can also include, e.g., one or more data communication programs, database management programs, device drivers, and the like.

The storage device 210 may also store one or more databases 226 required for operation of the RICA device 200. Such databases may include, for example, a database containing data concerning mix gradation, estimated density at each location on the mat after each pass of the roller, surface temperature of the mat during each roller pass, and/or GPS coordinates of the roller and the corresponding time. In some implementations, such data can be utilized, for example, to properly process sensor data from the sensor module and/or to generate compaction density estimates.

Referring again to FIG. 1, the roller machine 110 typically makes several passes on asphalt mat 130 during roadway construction. The asphalt mat 130 may include a portion 132 of a roadway to be compacted having a defined length, for example, three hundred (300) feet. Thus, locations can be identified on this portion 132 of the roadway, here indicated as locations A-B-C, C-D, and D-E in FIG. 1 which may each be approximately seventy-five (75) feet in length. These roadway locations may also be marked by the GPS device 136 during operation of the roller machine 110 and are associated with estimated densities of the roadway portion 132 during compaction operations. In particular, as the roller 120 of roller machine 110 makes a plurality of passes over the roadway section 132, the eccentric weights 122, 124 generate impacts and the responsive vibratory signals of the roller 120 are sensed by the accelerometer 124 as the roller 120 moves along roadway portion 132 and provided to the RICA processor 202. This vibratory data, in addition to temperature data obtained by the IR temperature sensors 124, is used to generate the compaction estimates as disclosed herein.

Figure 3A:
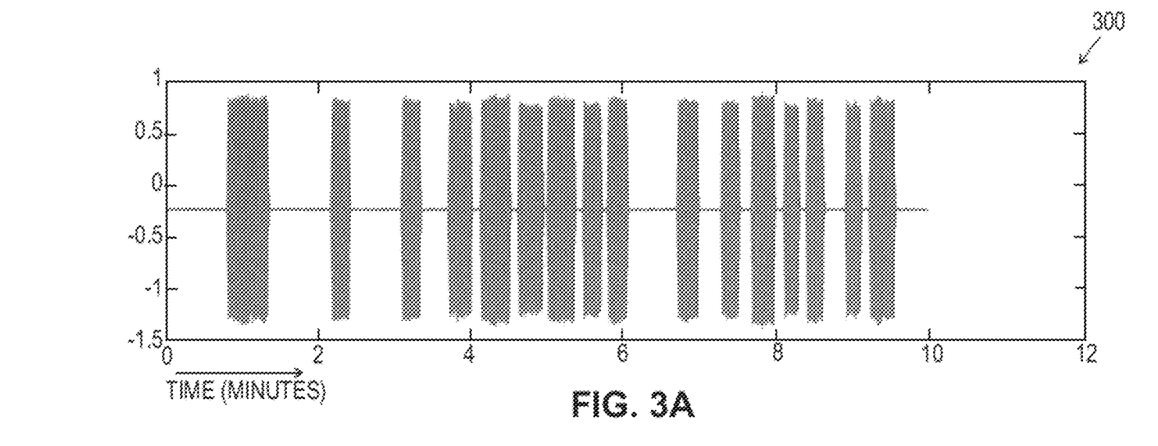
FIG. 3A is a graph illustrating vibrations of a roller drum of a roller machine such as that shown in FIG. 2 during each pass over a portion of pavement over time to compact asphalt pavement in accordance with some embodiments of the disclosure.
Figure 3B:
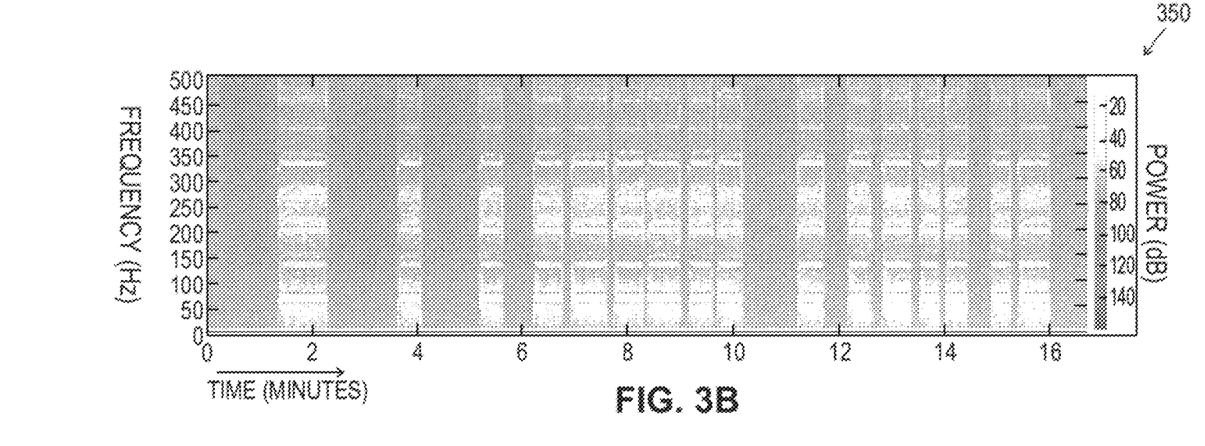
FIG. 3B is a spectrogram of the vibrations showing the frequency content (in Hertz) of the vibrations shown in FIG. 3A during the compaction process in accordance with some embodiments of the disclosure.

FIG. 3A is a graph 300 depicting the vibrations of the roller drum 120 of the roller machine 110 during each pass over a portion of pavement over time (here, from a starting point (zero; 0) to approximately 10 minutes) to compact asphalt pavement. FIG. 3B is a spectrogram 350 of the vibrations showing the frequency content (in Hertz) of the vibrations shown in FIG. 3A. The graph shows a vibratory compactor making sixteen (16) separate passes on a layer of asphalt mix.

FIG. 3B shows the fundamental frequency, i.e. the frequency of rotating eccentrics in the roller drum. The rotation of the eccentric mass results in one impulsive force for every rotation of the eccentric mass. Since the roller and the underlying pavement form a coupled system, both these systems exhibit a response to this input. The pavement layer undergoes viscoelastic-plastic deformation while the roller vibrates at the frequency of the input and its harmonics. An excitation frequency of 65 Hertz (Hz) will elicit a response at 65 Hz as well as the harmonics at 130 Hz, 195 Hz, 280 Hz, 325 Hz and 390 Hz. While the roller may exhibit a response at other frequencies, most of the vibrational energy of the response to the input is contained in the fundamental frequency and its harmonics. The power content of the vibration in a certain frequency band is related to the amplitude of the vibration and is expressed in decibels (db).

Figure 4A:
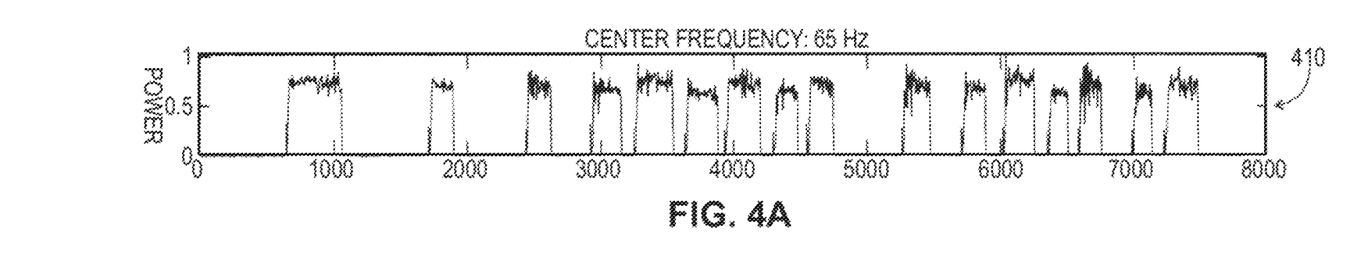
FIGS. 4A-4F are charts showing the vibration of the roller drum at different frequencies during the compaction process.
Figure 4B:
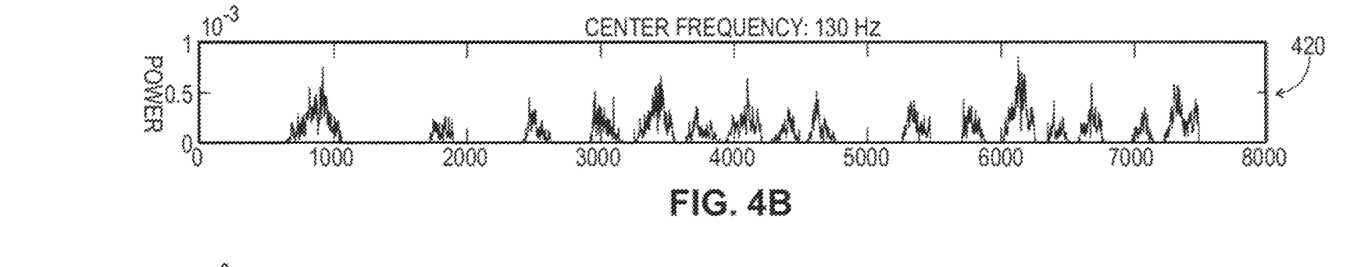
Figure 4C:
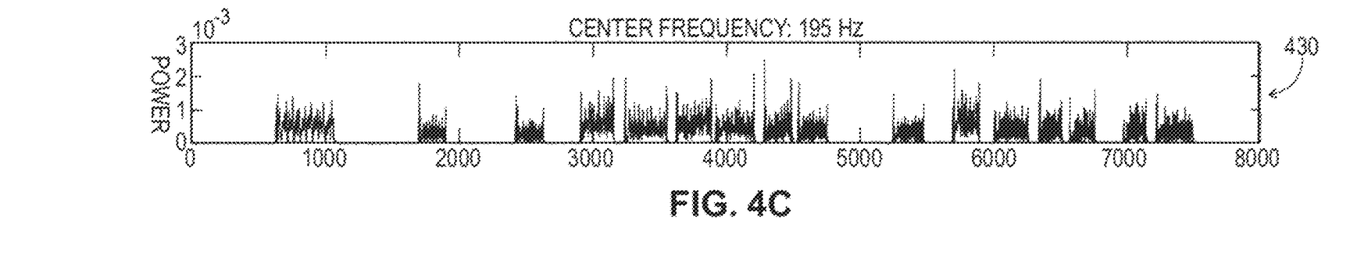
Figure 4D:
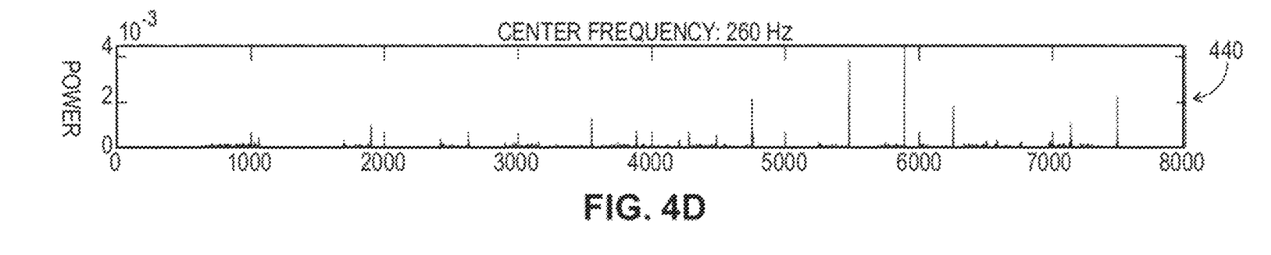
Figure 4E:
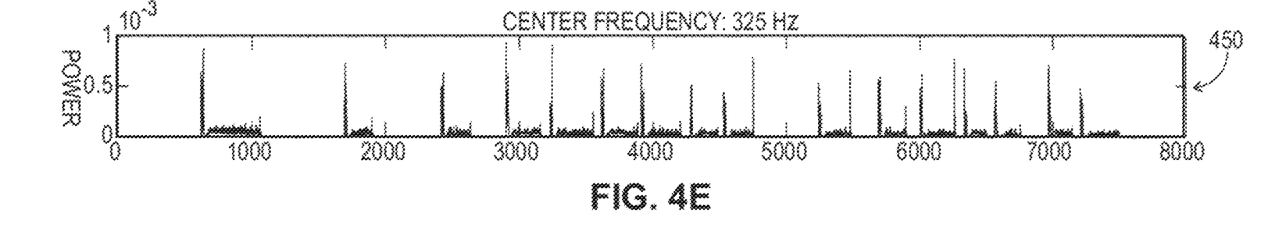
Figure 4F:
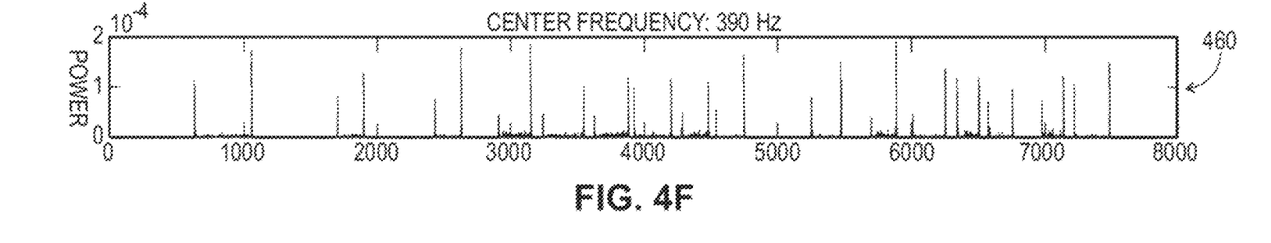

FIGS. 4A to 4F depict graphs 410-460 illustrating the power contained in select frequencies of drum vibrations of the roller machine. In particular, FIG. 4A is a graph 410 showing the power of the drum vibrations at a frequency of 65 Hertz (H); FIG. 4B is a graph 420 shows the power of the drum vibrations at a frequency of 130 Hertz (H); FIG. 4C is a graph 430 shows the power of the drum vibrations at a frequency of 195 Hertz (H); FIG. 4D is a graph 440 shows the power of the drum vibrations at a frequency of 280 Hertz (H); FIG. 4E is a graph 450 shows the power of the drum vibrations 450 at a frequency of 325 Hertz (H); and FIG. 4F is a graph 460 shows the power of the drum vibrations at a frequency of 390 Hertz (H).

Figure 5:
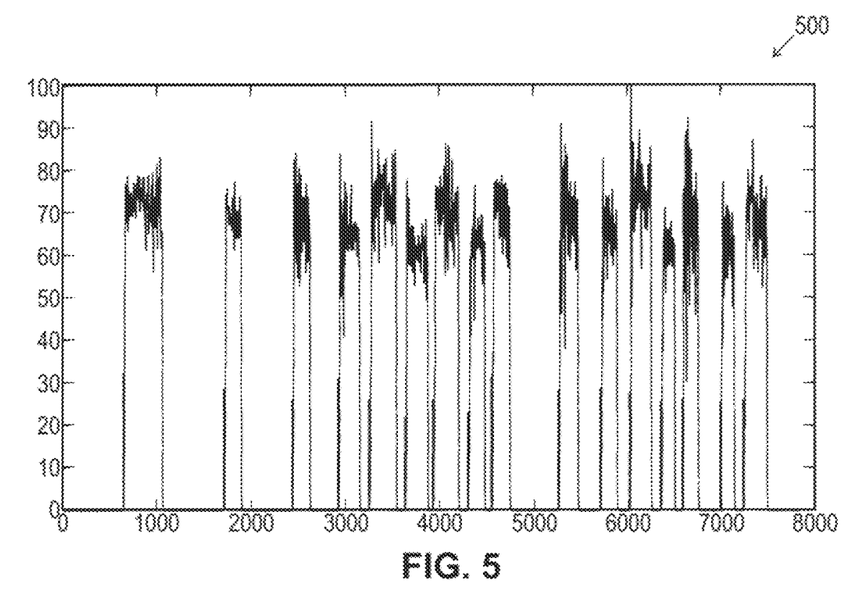
FIG. 5 is a chart illustrating the normalized power in each of the frequency bands depicted in FIG. 4.

FIG. 5 is a graph illustrating the normalized power in the fundamental frequencies 500 according to an embodiment. For each band of frequency, the vibration signal during the compaction of a test stretch of the pavement layer is analyzed and the minimum ($P_{min}$) and maximum ($P_{max}$) power levels are determined. Given the instantaneous power P, the normalized power is calculated as $100*(P-P_{min})/(P_{max}-P_{min})$.

Figure 6:
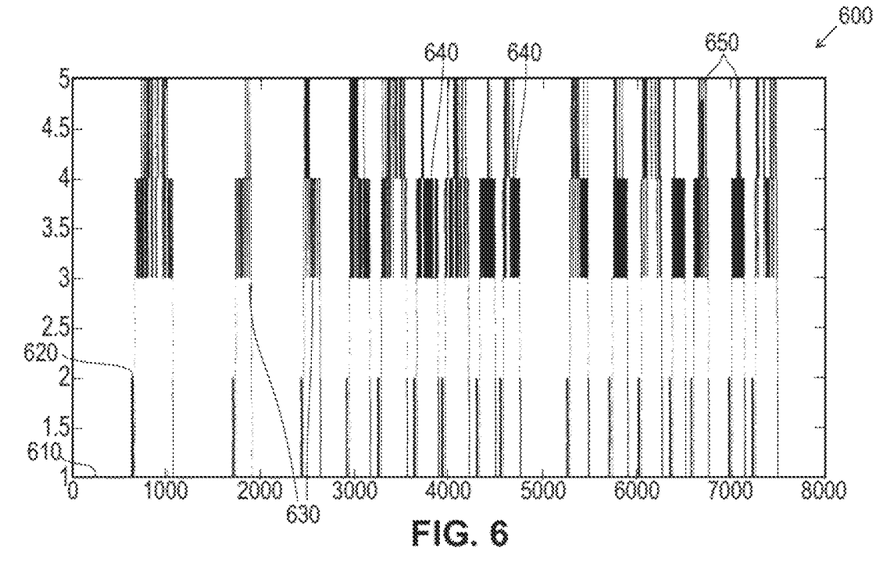
FIG. 6 is a chart showing the vibrations of the roller drum during compaction of the pavement layer classified into clusters representing different levels of compaction in accordance with embodiments of the disclosure.

FIG. 6 is a graph 600 grouping the vibratory response of the roller machine into clusters according to some embodiments. The normalized power in each frequency band is grouped into clusters representing vibrations reflective of increasing levels of compaction. There are many algorithms that can be used to group these vectors representing power in each frequency band, for example, k-means clustering, self-organizing maps, and the like. The lowest power level corresponds to the instance when the roller is on uncompacted asphalt mix and as a result, its response is muted. The highest power level indicates that the material is well compacted and as a result the roller exhibits increased vibrations at all frequencies. The precision of density estimates that is required dictates the number of clusters which are necessary. For example, four to six clusters are sufficient for accuracy within one percent (1%) of the actual density. Increasing the number of clusters increases the mis-classification errors, while too few clusters would limit the accuracy that is achieved. In some embodiments, a low pass filter is used to interpolate between the density estimated from the clusters at each subsequent step in time. In the example shown in FIG. 6, the vibratory clusters include a first cluster 610, second cluster 620, third cluster 630, fourth cluster 640 and fifth cluster 650.

Figure 7A:
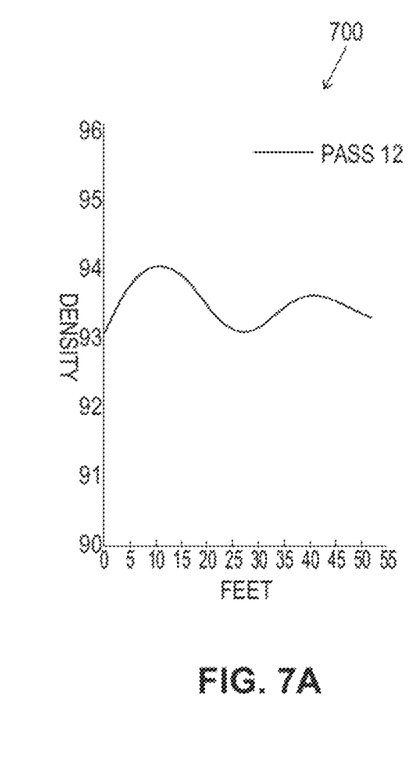
FIGS. 7A, 7B and 7C are charts illustrating the estimated density in accordance with embodiments of the disclosure.
Figure 7B:
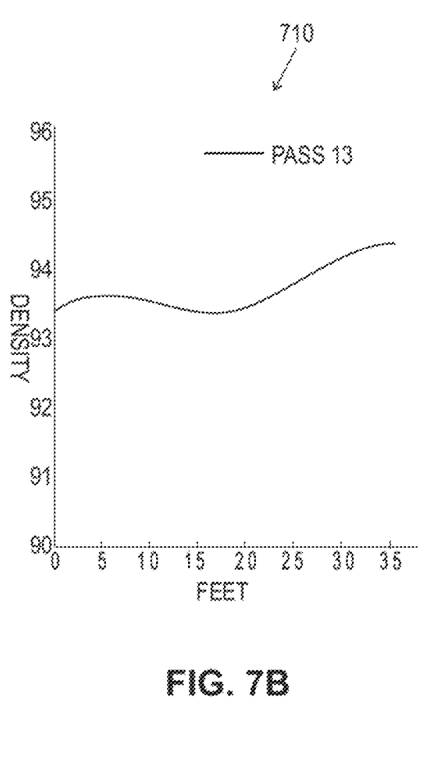
Figure 7C:
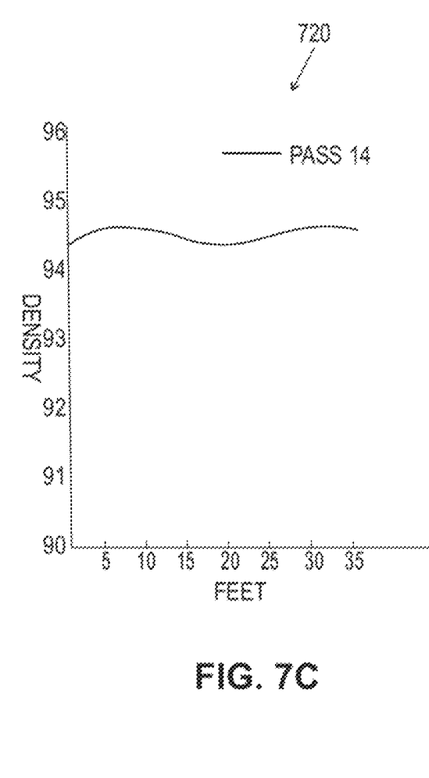

FIGS. 7A, 7B and 7C illustrate graphs of density estimates 700, 710 and 720, respectively, of three passes of the roller machine using the cluster information of FIG. 6. Specifically, in some implementations, the RICA device 200 monitors the fundamental frequency of vibrations of the roller drum during compaction as the roller drum moves in both the forward and backward directions over the pavement, filters the accelerometer data from one or more accelerometers by using a bank of filters, and extracts the average vibrational energy at each of the harmonics. Next, the RICA device 200 normalizes the average energy of the harmonics in the accelerometer data and groups the energy into a pre-specified or predetermined number of groups. In some implementations, clustering techniques are utilized to group the energy data into five (5) different groups of vibrations, as shown in FIG. 6. A smoothing function may then be used to relate the five groups of vibrations into an estimated level of compaction. Next, the RICA device 200 relates the estimated level of compaction to one or more density measurements determined from cores that have been extracted from known locations so that the estimated level of compaction can be expressed as a percentage Theoretical Maximum Density (% TMD).

FIG. 8 illustrates display screen output data 800 which may be provided to an operator of a vibratory compactor 110 (See FIG. 1) on a display screen 116 of a RICA device 112 retrofit to the vibratory compactor in accordance with the disclosure. In some embodiments, the display screen data 800 includes a speedometer 802 or speed indicator that indicates the speed of the vibratory compactor, a mat temperature gauge 804 indicating mat temperature, and a density percentage readout 806 indicating the current density percentage. The operator may use control buttons 808 and 810 to toggle between showing data associated with a first roller and with a second roller, respectively, of the vibratory compactor. For a specified frequency of the eccentrics, the roller speed determines the spacing of the impacts on the asphalt mat. Speeds greater than the rated speed will increased the spacing between subsequent locations on the mat and will result in non-uniform compaction. Low speeds will decrease the spacing between subsequent impact locations and can lead to over-compaction and damage to the pavement. Thus, the speed indicator 802 and the mat temperature indicator 804 help the roller operator to operate the roller within the desired operating range, which results in minimizing or reducing the variability in compaction arising from operator actions (or operator errors).

The Temperature Gauge 804 also includes the range of temperatures necessary for different roller operations. For example, the asphalt mat must be between 270-350 degrees Fahrenheit (or about 132-154.5 degrees Celsius) for breakdown (BD) rolling. Similarly, the asphalt mat must be between 200-250 degrees Fahrenheit (93-121 degrees Celsius) for intermediate (IR) rolling, and between 130-160 degrees Fahrenheit (54-71 degrees Celsius) for finish rolling, respectively. These temperature ranges can be input into the computer system for each job or compaction project to provide easy guidance to the operator of the vibratory roller concerning when the asphalt mat is ready for compaction.

The graphs 812 and 814 display indications of the compaction achieved over a roller pass. In some implementations, the density estimates during each roller pass are shown in the form of a color-coded map. Each map shows the path of the roller and the density estimated over the pass. The operator can step through the previous passes to study the coverage of the asphalt mat to make a determination as to whether the roller has compacted every location on the mat, and view the level of compaction that was achieved. In addition, the map also provides a visual indicator of the uniformity of compaction as in some implementations locations with similar density estimates will be display in the same or identical colors. In addition, each of the graphs 812 and 814 can also display the average density estimated on that particular pass and the uniformity of compaction [=(1/(3*standard deviation)*100].

In some embodiments, the toggle buttons 808 and 810 can be used by a first operator to obtain the mat temperature and density estimates of a second RICA equipped roller machine being operated by a second operator that may be operating in tandem with the first roller (operated by the first operator). For example, a first roller machine outfitted with a first RICA device being operated by a first operator may be used to perform a breakdown operation, or a first compaction pass of the roller machine over a freshly placed hot asphalt mat. Next, a second operator operating a separate, second roller machine outfitted with a second RICA device may be tasked with performing a compaction and finish operation over the same portion of the roadway. In some embodiments, the second roller operator may utilize the second RICA device to obtain the estimated level of compaction data from the first RICA device concerning the operation performed by the first operator and first roller machine. The obtained estimated level of compaction data received from the first RICA device can then be used to display an estimated level of compaction on the display screen of the second RICA device so that the second operator of the second roller machine can make a determination, for example, of how fast the second roller machine should proceed and/or how much time the second roller machine should spend on a particular portion of roadway to achieve the desired compaction results. Thus, the ability to see in real-time the compaction details of the second roller machine along with the estimated level of compaction from the first roller machine advantageously helps the second operator to coordinate the performance of the first and second rollers which are operating in tandem to improve productivity.

Figure 9:
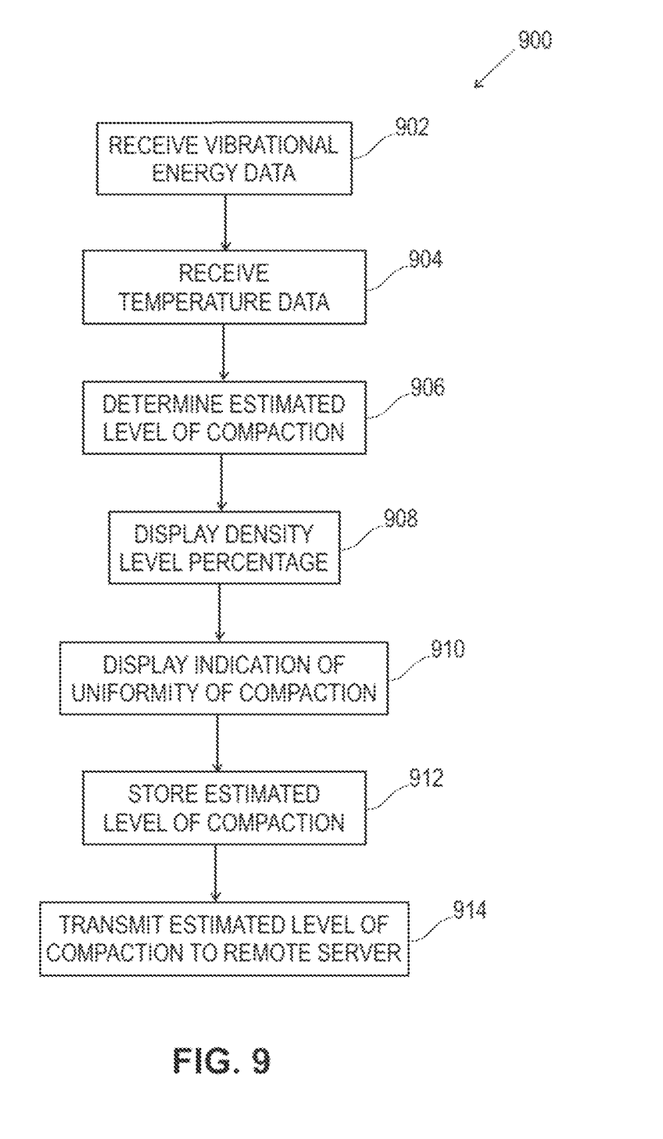
FIG. 9 is a flowchart illustrating a method for providing an estimate of the level of compaction of pavement materials in real time to an operator of a roller machine in accordance with embodiments of the disclosure.

FIG. 9 is a flowchart 900 illustrating a method for providing an estimate of the level of compaction of pavement materials in real time to an operator of a roller machine in accordance with some embodiments. In some embodiments, a Retrofit Intelligent Compaction Analyzer (RICA) processor of a RICA device retrofit to a roller machine receives 902 vibrational energy data from a sensor module. The vibrational energy data corresponds to impact responses of at least one drum of the roller machine during compaction of a pavement material over a section of pavement. The RICA processor also receives 904 temperature data from the sensor module, which may be generated by at least one infrared temperature sensor over the section of pavement. The RICA processor next determines 906 an estimated level of compaction in real time of the section of pavement based on the vibrational energy data, pavement material characteristics data and the temperature data, and then displays 908 a density level percentage of the section of pavement on a display device for viewing by an operator of the roller machine, wherein the density level percentage is based on the estimated level of compaction. In some embodiments, the RICA processor also displays 910 an indication of the uniformity of compaction achieved by a roller pass of the roller machine over the section of pavement on the display device.

In some embodiments, the RICO processor determines 906 the estimated level of compaction by monitoring the fundamental frequency of vibrations of a roller drum of the roller machine during compaction as the roller drum moves in both a forward and a backward direction over the pavement, filtering accelerometer data from at least one accelerometer to extract an average vibrational energy at each of the harmonics, normalizing the average energy of the harmonics in the accelerometer data, and grouping vibrational energy into a predetermined number of vibratory clusters. In addition, in some implementations the RICA processor relates data associated with the vibratory clusters into an estimated level of compaction by using a smoothing function. In some embodiments, the RICA processor relates the estimated level of compaction into one or more density measurements determined from cores extracted from known locations, and then expresses the estimated level of compaction as a percentage Theoretical Maximum Density (% TMD).

Referring again to FIG. 9, in some embodiments the process also includes the RICA processor at least one of storing 912 the estimated level of compaction in the storage device and transmitting 914 the estimated level of compaction to a remote server. In some implementations, the RICA processor may also receive geospatial location data of the vibratory roller machine as it traverses the section of pavement from a GPS device, associate the geospatial location data with the estimated level of compaction data, and then transmit the geospatial location data and associated estimated level of compaction data to a remote computer. In addition, the RICA processor may next store the geospatial location data and the associated estimated level of compaction data in the storage device.

Thus, systems and methods disclosed herein advantageously provide a Retrofit Intelligent Compaction Analyzer (RICA) device that can be easily retrofit to existing roller machines, such as vibratory compactor vehicles, and provide real-time compaction data to the operator of the roller machine. The roller machine operator can beneficially use the estimated level of compaction information in real-time during roadway construction and act accordingly. For example, if the level of compaction information indicates that required standards are not met then the roller machine operator can take corrective steps, such as making another pass of the drum of the roller machine over a section of roadway, that he or she deems necessary to achieve a desired quality level of compaction during construction of the pavement. Such action advantageously saves time and money as compared to having to rip up a portion of a roadway that is later found to be deficient.

As used herein, the term "computer" should be understood to encompass a single computer or two or more computers in communication with each other.

As used herein, the term "processor" should be understood to encompass a single processor or two or more processors in communication with each other.

As used herein, the term "memory" or "storage device" should be understood to encompass a single non-transitory memory or storage device or two or more memories or storage devices.

As used herein, a "server" includes a computer device or computer system that responds to numerous requests for service from other electronic devices.

The above descriptions and illustrations of processes herein should not be considered to imply a fixed order for performing the process steps. Rather, the process steps may be performed in any order that is practicable, including simultaneous performance of at least some steps and/or omission of elements or steps.

Although the present disclosure has been described in connection with specific example embodiments, it should be understood that various changes, substitutions, and alterations apparent to those skilled in the art can be made to the disclosed embodiments without departing from the spirit and scope of the disclosure.

What is claimed is:

1. A method for providing an estimate of the level of compaction of a layer of pavement materials in real time, comprising:
   receiving, by a Retrofit Intelligent Compaction Analyzer (RICA) processor from a sensor module, vibrational energy data corresponding to impact responses of at least one drum of a roller machine during compaction of a pavement material over a section of pavement;
   receiving, by the RICA processor from the sensor module, temperature data generated by at least one infrared temperature sensor over the section of pavement;
   determining, by the RICA processor, an estimated level of compaction in real time of the section of pavement by:
      monitoring the fundamental frequency of vibrations of the at least one drum of the roller machine during compaction as the at least one roller drum moves in both a forward and a backward direction over the section of pavement;
      extracting an average vibrational energy at each of the harmonics of the fundamental frequency by filtering accelerometer data from at least one accelerometer;
      normalizing the average vibrational energy of the harmonics in the accelerometer data; and
      grouping the average vibrational energy at the fundamental frequency and the harmonics into a predetermined number of vibratory clusters reflecting increasing levels of compaction; and
   displaying, by the RICA processor on a display device, a density level percentage of the section of pavement based on the estimated level of compaction for viewing by an operator of the roller machine.

2. The method of claim 1, further comprising displaying, by the RICA processor on the display device, an indication of the uniformity of compaction achieved by a roller pass of the roller machine over the section of pavement.

3. The method of claim 1, further comprising displaying, by the RICA processor on the display device, an indication of a mat temperature over the section of pavement.

4. The method of claim 1, further comprising relating, by the RICA processor utilizing a smoothing function, data associated with the vibratory clusters into an estimated level of compaction.

5. The method of claim 4, further comprising:
   relating, by the RICA processor, the estimated level of compaction into one or more density measurements determined from cores extracted from known locations; and
   expressing, by the RICA processor, the estimated level of compaction as a percentage Theoretical Maximum Density (% TMD).

6. The method of claim 1, further comprising at least one of:
   storing, by the RICA processor in a storage device, the estimated level of compaction; and
   transmitting, by the RICA processor, the estimated level of compaction to a remote server.

7. The method of claim 1, further comprising:
   receiving, by the RICA processor from a GPS device, geospatial location data of the roller machine as it traverses the section of pavement;
   associating, by the RICA processor, the geospatial location data with the estimated level of compaction data; and
   transmitting, by the RICA processor, the geospatial location data and associated estimated level of compaction data to a remote computer.

8. The method of claim 7, further comprising storing, by the RICA processor in a storage device, the geospatial location data and the associated estimated level of compaction data.

9. The method of claim 1, further comprising:
   receiving, by the RICA processor from a second RICA processor of a second RICA device associated with a second roller machine, a second estimated level of compaction associated with operation of the second roller machine over the section of pavement; and
   displaying, by the RICA processor on the display device based on the second estimated level of compaction, a second density level percentage for use by the operator of the roller machine to determine how to achieve a desired compaction level.

10. A Retrofit Intelligent Compaction Analyzer (RICA) device for providing an estimate of the level of compaction of a layer of pavement materials in real time comprising:
    a RICA processor;
    a communication device operably connected to the RICA processor;
    a display device operably connected to the RICA processor;
    a sensor module operably connected to the RICA processor; and
    a storage device operably connected to the RICA processor, wherein the storage device stores processor executable instructions which when executed cause the RICA processor to:
       receive vibrational energy data from the sensor module, the vibrational energy data corresponding to impact responses of at least one drum of a roller machine during compaction of a pavement material over a section of pavement;

receive temperature data from the sensor module, the temperature data generated by at least one infrared temperature sensor over the section of pavement;

determine an estimated level of compaction in real time of the section of pavement by:
- monitoring the fundamental frequency of vibrations of the at least one drum of the roller machine during compaction as the at least one roller drum moves in both a forward and a backward direction over the section of pavement;
- extracting an average vibrational energy at each of the harmonics of the fundamental frequency by filtering accelerometer data from at least one accelerometer;
- normalizing the average vibrational energy of the harmonics in the accelerometer data; and
- grouping the average vibrational energy at the fundamental frequency and the harmonics into a predetermined number of vibratory clusters reflecting increasing levels of compaction; and display a density level percentage of the section of pavement on the display device for viewing by an operator of the roller machine, wherein the density level percentage is based on the estimated level of compaction.

11. The apparatus of claim 10, wherein the storage device stores further processor executable instructions which when executed cause the RICA processor to display an indication of the uniformity of compaction achieved by a roller pass of the roller machine over the section of pavement on the display device.

12. The apparatus of claim 10, wherein the storage device stores further processor executable instructions which when executed cause the RICA processor to display an indication of a mat temperature over the section of pavement on the display device.

13. The apparatus of claim 10, wherein the storage device stores further processor executable instructions which when executed cause the RICA processor to at least one of:
- store the estimated level of compaction in the storage device; and
- transmit the estimated level of compaction to a remote server.

14. The apparatus of claim 10 further comprising a GPS device operably connected to the RICA processor, and wherein the storage device stores further processor executable instructions which when executed cause the RICA processor to:
- receive geospatial location data of the roller machine from the GPS device as it traverses the section of pavement;
- associate the geospatial location data with the estimated level of compaction data; and
- transmit the geospatial location data and associated estimated level of compaction data to a remote computer.

15. The apparatus of claim 14, wherein the storage device stores further processor executable instructions which when executed cause the RICA processor to store the geospatial location data and the associated estimated level of compaction data in the storage device.

16. The apparatus of claim 10, wherein the storage device stores further processor executable instructions which when executed cause the RICA processor to:
- receive a second estimated level of compaction associated with operation of a second roller machine over the section of pavement from a second RICA processor of a second RICA device associated with a second roller machine; and
- display a second density level percentage on the display device based on the second estimated level of compaction for use by the operator of the roller machine to determine how to achieve a desired compaction level.

* * * * *